(12) United States Patent
Buss

(10) Patent No.: US 7,042,234 B2
(45) Date of Patent: May 9, 2006

(54) SOIL MATRIC POTENTIAL AND SALINITY MEASUREMENT APPARATUS AND METHOD OF USE

(75) Inventor: Peter Buss, Woodforde (AU)

(73) Assignee: Sentek Pty Ltd, South Australia (AU)

(*) Notice: Subject to any disclaimer, the term of this patent is extended or adjusted under 35 U.S.C. 154(b) by 0 days.

(21) Appl. No.: 10/737,717

(22) Filed: Dec. 16, 2003

(65) Prior Publication Data
US 2004/0145379 A1    Jul. 29, 2004

(30) Foreign Application Priority Data
Dec. 16, 2002 (AU) .............................. 2002953346

(51) Int. Cl.
*G01R 27/26* (2006.01)
(52) U.S. Cl. ..................... 324/664; 324/658
(58) Field of Classification Search .......... 73/73; 137/78.3; 324/690, 696, 658, 664
See application file for complete search history.

(56) References Cited

U.S. PATENT DOCUMENTS

| | | | |
|---|---|---|---|
| 3,847,351 A | 11/1974 | Hasenbeck | 239/63 |
| 4,137,931 A | 2/1979 | Hasenbeck | 137/78.3 |
| 4,216,789 A | 8/1980 | Hasenbeck | 137/78.3 |
| 4,561,294 A | 12/1985 | Wilkinson | 73/73 |
| 4,655,076 A * | 4/1987 | Weihe et al. | 73/73 |
| 5,418,466 A | 5/1995 | Watson et al. | 324/668 |
| 5,445,178 A * | 8/1995 | Feuer | 137/1 |
| 5,898,310 A * | 4/1999 | Liu | 324/690 |
| 6,014,029 A | 1/2000 | Soto et al. | 324/664 |
| 6,289,725 B1 | 9/2001 | Hubbell et al. | 73/73 |
| 6,441,622 B1 * | 8/2002 | Wrzesinski et al. | 324/643 |
| 6,445,565 B1 * | 9/2002 | Toyoda et al. | 361/303 |
| 2002/0167412 A1 * | 11/2002 | Cuming | 340/602 |

FOREIGN PATENT DOCUMENTS

| | | |
|---|---|---|
| AU | 728070 | 2/1998 |
| AU | 761288 | 12/1999 |
| WO | WO 97/01090 | 1/1997 |
| WO | WO 98/04915 | 2/1998 |

OTHER PUBLICATIONS

M.A. Hilhorst et al; A Dielectric Tensiometer; Agricultural Water Management, 13 (1988) 411-415.

* cited by examiner

*Primary Examiner*—Walter Benson
(74) *Attorney, Agent, or Firm*—Klauber & Jackson

(57) ABSTRACT

A soil parameter measurement arrangement includes a capacitive based soil moisture and salinity sensor, a predetermined moisture migration medium located in a volume adjacent said sensor so that the medium substantially occupies the field of influence of said sensor. The medium is in moisture communication with the soil to be measured, and said sensor is adapted to measure and produce data representative of the volumetric water content of said medium. A sensor data processing means determines both the soil moisture and salinity of said medium. By using the measured volumetric soil moisture content and the moisture release curve of the medium, it is possible to derive the matric potential of the soil. The measured salinity of the medium corresponds to the salinity of the soil that is in moisture communication with the medium.

15 Claims, 6 Drawing Sheets

SOIL MATRIC POTENTIAL AND SALINITY MEASUREMENT APPARATUS AND METHOD OF USE

This invention relates to measuring soil matric potential and soil salinity.

BACKGROUND

The retention and movement of water in soils, its uptake and translocation in plants and its loss to the atmosphere are all energy-related phenomena. All substances including water have a tendency to move or change from a state of higher to one of lower energy. Water movements in soils will generally be from a zone where the energy level of the water is high (wet soil) to one where the energy level is low (dry soil). If the pertinent energy levels at various points in the soil are known, the direction of water movement can be predicted.

Three important forces affect the energy level of soil water.

First adhesion, or the attraction of the soil solids (matrix) for water, provides a matric force (responsible for the phenomenon of adsorption and capillarity) that markedly reduces the energy state of the adsorbed water molecules. To a lesser extent the forces of cohesion which describes the attraction of water molecules to each other lowers the energy state. Together these forces produce a suction force within soil.

Second, the attraction of ions and other solutes towards water, result in osmotic forces, that tend to reduce the energy level in the soil solution. Osmotic movement of pure water across a semipermeable membrane into a soil solution is evidence of the lower energy state of the soil solution.

The third major force acting on soil water is gravitational force, which tends to pull water downward. The energy level of water at a given elevation in the soil profile is thus higher than that of water at a lower elevation. This difference in energy level causes water to flow downward.

Energy levels of soil water are usefully compared with that of a sample of pure water outside the soil in an environment that is maintained at standard pressure, temperature, and elevation levels. The difference in energy levels between the pure water and that of soil water is termed soil water potential.

Soil water (matric) potential is always negative, because it requires a force to draw water from the soil matrix implying that the water is moving from a higher energy state towards the lower energy state of pure water.

Every soil type has the ability to retain a specific volume of water due to its texture and pore volume or soil porosity (empty spaces between soil colloids). The matric force or the matric potential ($\psi$) which results from the phenomena of adhesion (or adsorption) and of capillarity, influences soil moisture retention or the total amount of stored soil water as well as soil water movement.

The volume of water held in soil that has been watered and has become fully drained (the point in time, where maximum amount of water is held against gravity) is called the field capacity of that soil type.

Therefore, a fine textured soil type such as clay contains by its physical nature, numerous small pores and capillary channels in which water can be retained against the pull of gravity because of matric forces exerted by the soil on soil water. Contrastingly, coarse, sandy soil has fewer, but larger pores in which lower matric forces contribute to lower soil water storage potential at field capacity.

The size and amount of pores in the soil type and a given soil water content at a point in time, dictates the matric force by which water is bound to the soil particles in that type of soil. This matric force is equivalent to the negative tension (suction–matric potential), that plant roots have to overcome to remove water from the soil for uptake.

The permanent wilting point is defined as the water content at which plants can no longer extract soil water at a rate sufficient to meet physiological demand. The physical demand of the plant is determined by the loss of water to the atmosphere (evapotranspiration) and at wilting point plants wilt and die. The permanent wilting point is generally reached at a matric potential of −15 bars.

A primary practical use of field capacity and wilting point concepts is the determination of a plant available soil water range (PASW). Soil water storage available for plant use is generally calculated as being between field capacity and permanent wilting point.

Different soils can have greatly differing wetness versus matric potential (tension or suction) relationships (e.g., a sandy soil may retain less than 5% water content at −15 bar matric potential, whereas a clayey soil may retain three times as much). Clearly, the more compacted a soil compound is, the less capacity there exists to retain soil moisture because of reduced pore volume or porosity with the converse also being true. Therefore, different absolute amounts of water are stored in different soil textures.

The concept of plant available soil water storage is an important factor in the determination of irrigation amounts for a cropped field or other soil-plant system. For practical purposes, irrigation amounts in excess of field capacity are lost. This is so because the excess soil water percolates away, and, this should be avoided in the interest of water resource conservation. There is also a potential for the leaching of beneficial soluble salts and chemicals from the zone within which the crop can draw soil water containing those salts and chemicals.

The relation between the volumetric soil water content (%) (which is the percentage amount of soil water retained by the soil on a volume basis) and soil water tension (suction, matric potential) is referred to as the water retention characteristic and this relation can be described mathematically using a soil water release curve.

Gravimetric soil water content $W=(Mw-Md)/Md (g\ g^{-1})$

Where

Mw=wet mass of soil core (g)

Md=dry mass or soil core (g)

Bulk density $\rho = Md/V\ cm^{-3}$

Volumetric water content $\theta v = W\rho 1$

A tensiometer is but one of a number of devices used to measure the force by which the soil retains the water which in turn is related to how difficult the root system of a plant finds it to extract water from the soil. Although there are many other apparatus, tensiometers are typically used by farmers and plant and soil researchers for the measurement of this soil characteristic.

The parameter measured by a tensiometer is provided in units of centibars (cb) and millibars (mb) and is known as the 'soil matric potential' ($\psi m$). In recent years the metric equivalent (S. I. units) of kilopascals (kPa) has also been adopted as a measurement unit for soil matric potential. The soil matric potential indicates the degree to which the plant needs to create an energy differential in its root system so as to initiate moisture migration from the soil into its root system.

Tensiometers provide their measurement, as mentioned, in centibars where 100 centibars equals one bar. The higher the centibar reading, for example 40 cb, the harder it is for the plant root system to extract moisture from the surrounding soil and conversely the lower reading, for example 10 cb, the easier it is.

Tensiometers are relatively simple devices comprising a hollow tube with a water porous but air impermeable ceramic tip (specified to a certain air entry value, say 1 bar) forming the lower end of an elongate water impervious tube. The tube is filled with water and sealed with a top cap. A vacuum gauge is attached to the top cap and the small volume of air above the water in the tube is used to measure the pressure inside the tube. The tube is then buried in a prepared hole in the soil with the ceramic tip in close contact with the soil at a desired depth within the soil profile.

When the matric potential of the soil is lower (more negative) than the equivalent pressure inside the tensiometer, tip which occurs when plant roots draw water from the soil surrounding the ceramic tip of the tensiometer, water moves from the tensiometer along a potential energy gradient to the soil through its saturated porous cup. This action creates suction or negative tension, which is sensed by the pressure gauge as an increase in negative pressure (vacuum) in the top part of the tube. Water flow into the soil continues until equilibrium is reached and the suction outside the tensiometer equals the soil matric potential. After rainfall or irrigation events, pore spaces within the soil fill with water. Water will then migrate back through the ceramic tip into the tensiometer tube due to now lower matric forces, which in turn lowers the negative pressure (vacuum) of the measurement instrument.

The exchange of water between the tensiometer and the soil it is located within works only to a specified negative pressure (suction, matric potential) of the ceramic tip. A ceramic tip with an air entry value of 80 cb experiencing a matric potential of 100 cb will allow air to migrate into the tensiometer tube. As soon as this occurs, the negative pressure of the instrument will rapidly drop to a value close to 0 cb, and the measurement of the instrument will not reflect the real prevailing matric potential of 100 cb and hence the instrument is not useable in such conditions. To rectify this situation, the tensiometer tube has to be re-filled with water. A hand vacuum pump attached to the top of the tensiometer tube has to be operated to draw soil water through the ceramic tip of the tensiometer to purge any trapped air bubbles within the ceramic tip with water. This corrective service will again establish the exchange of water only (in and out) between soil and the tensiometer tube water reservoir so that proper measurements can be taken by the tensiometer.

Installation of tensiometers according to the following guidelines is typical:

Installed shortly after plant emergence, between healthy average sized plants in a site that represents a soil type average for the planted crop.

One tensiometer is commonly installed at a depth of maximum root density, say 30 cm and another may be placed near the bottom of the active rootzone, say 60 cm, making up one profile measurement station. These depths may vary according to crop type.

One or two stations per crop of the same age and variety are commonly used. Other stations may be used to reflect changes in field topography. Readings should be taken at the same time each day preferably in the morning, noting that diurnal fluctuation in soil matric potential may require more than one reading per day.

At minimum readings should be taken every two days in medium textured soils and every day in light textured soils.

It is advisable to log tensiometer reading at a 30-minute time interval on a continuous basis so as to generate sufficient data upon which to base irrigation management decisions. Loggable tensiometers are fitted with a pressure transducer instead of a manual pressure gauge.

Unfortunately, tensiometers have a variety of problems, including those described earlier and operate within a limited range of measurement, at best 0 cb to 80 cb. Tensiometers require specialised set up procedures and include the use of degassed water. Air tends to permeate the ceramic of the sensor especially when soil tension exceeds the air entry value. In sub-zero temperatures the water in the apparatus freezes rendering it inoperable. The device is fragile and requires continual maintenance despite its simple construction. The type of maintenance includes topping up with degassed water, vacuum pumping to purge air from the device and the need to add algacide periodically to the water in the tube so as to prevent algae build up.

Furthermore a tensiometer itself attracts plant roots in its immediate vicinity because it is a constant source of moisture. The latter of the abovementioned problems can skew the relevance of the measurements taken, as the field measurement point of the tensiometer may now have a significantly larger root length density per soil volume than the surrounding crop.

A tensiometer is limited in its ability to determine matric potential, which must lie between 0 kPa (saturation), and 80 kPa (dry). This is due mainly to the fact that the vacuum gauge or manometer measures a partial vacuum relative to the external atmospheric pressure and with the general failure of water columns in macroscopic systems to withstand tensions exceeding 1 atmosphere or 1 bar or 100 kpa. Some agricultural crops are subjected to a managed soil moisture condition exceeding this threshold and hence tensiometers cannot be reliably used for these applications.

Matric potential is described herein as a force per unit area or pressure which has units of pascals or mega-pascals (1 Mpa=10 bars, 100 kPa=1 bar). One atmosphere is equivalent to the pressure exerted by a column of water 100 cm high.

There are also reading range problems associated with soil texture. For example, the hydraulic contact between a coarse sand matrix and the tensiometer tip is more easily interrupted than in heavy textured soils (below 85 kPa).

A tensiometer is not depth compensated. The tensiometer equation is:

$$\psi_m = \psi_{gauge} + (z_{gauge} - z_{tip})$$

The vertical distance from the gauge plane $z_{gauge}$ to the tip $z_{tip}$ must be added to the matric potential measured by the gauge (expressed as a negative quantity) to obtain the matric potential at the depth of the tip. This accounts for the positive head at the depth of the ceramic tip exerted by the overlaying tensiometer water column. For example: −3 cb needs to be added for each 30 cm of instrument length.

The accuracy of the tensiometer is no better than +/−1.2 kPa in wet conditions. A higher resolution at the "wet end" would allow the tension measurement technology to be applicable to other markets such as nurseries and greenhouses. Container media consisting mostly of materials such as peat, bark, sand, perlite and vermiculite are combined to form a mix, which holds a large percentage of volumetric water content. However a matric potential measurement of 8–10 kPa indicates that the mixture is a relatively dry medium.

Tensiometers cannot be used immediately after installation. The sensing tip has to be soaked in degassed water for a couple of days. Letting the tip dry out renders the instrument useless for measurement until rewatered.

Owing to the hydraulic resistance of the tensiometer tip (cup) and the surrounding soil and the contact zone between tip and soil, the tensiometer response of some instruments may lag behind suction changes in the soil, ie there exists a finite response time.

Tensiometers are not frost tolerant. If water freezes inside the tube, the expansion caused through ice formation can potentially destroy the instrument.

Installation of the instrument can cause problems, especially deep installation where the tensiometer tip has to be pushed into a slightly undersized hole at the bottom of a larger access hole. The tip can easily break off while being pushed into the lower and unseen undersized hole.

Air bubbles frequently appear inside the water-filled tube connecting the porous tip to the manometer. This occurs because of the reduced solubility of gases at lower hydrostatic pressure (as well as higher temperatures) and also because of the diffusion of gases from the air phase of the unsaturated soil trough the porous walls of the tensiometer tip. Occurrences of these bubbles do not immediately negate the measurement but reduces its sensitivity.

Therefore tensiometers require continual labour intensive maintenance. There is an ongoing risk of not being able to take readings from the Tensiometer because the instrument has ceased to work due to lack of adequate maintenance.

One tensiometer providing one measurement point is not very useful to indicate soil moisture profile dynamics throughout the crop's rootzone. It is common practice to use 3 to 4 individual tensiometers to present measurement points throughout the soil profile, which can triple or quadruple the already intensive manual maintenance requirements.

Tensiometers are unable to measure rising and falling levels of salinity, since the wall of the tensiometer' porous cup is permeable to both water and solutes. Solutes in the soil solution diffuse freely into the cup so that the water inside the tensiometer tends to assume the same solute composition and concentration (osmotic potential) as the surrounding soil water.

Instrument precision and accuracy to measure matric potential for the purpose of irrigation scheduling of commercial crops is critically important to a crop grower, as the economic return of their enterprise depends on the quality of these measurements.

Furthermore is the knowledge that at a particular soil water tension the crop will be going into water stress. Clearly the ultimate aim is to provide appropriate crop management information based on accurate tensiometer readings, as these will be used to make critical irrigation management decisions.

Not only are the water contents and its associated matric potential important for irrigation scheduling but so is the management of fertilizer concentration in the soil. More particularly it is of primary importance that there be an availability of beneficial solutes in the soil water (as provided by fertilizer) at a depth that is in the active uptake zone of the crop root system. Fertilizer salts are easily leached from the rootzone in humid environments through rainfall or in arid environments through over irrigation practice.

Harmful salt concentrations can built up naturally in surface soils of arid and semi-arid regions through weathering of rocks and minerals and insufficient rainfall to flush these salts from the upper soil layers. Under-irrigation practices, where irrigation water salts and fertilizer salts accumulate in the rootzone will also potentially become damaging to crop health.

In poorly drained soils downward movement of the irrigation water and fertilizer salts to the groundwater is impaired, leaving salts in the soil to be brought up later to the surface as the irrigation water evaporates. A saline soil is thus created. Historically, large increases in worldwide food crop requirements have been satisfied by expanded irrigation practices. However, in many areas the need for good drainage was overlooked and the process of salinization has been accelerated.

Salt concentrations can also be concentrated in the rootzone through rising watertables or horizontally moving fossil salt deposits moving over impervious geological layers. These may ultimately rise to the soil surface in the low-lying parts of the landscape forming saline seeps.

In arid areas of the world where evaporation is high, the salt build-up in irrigated soils must be monitored to ensure successful plant production and to stop fertilizer leakage into waterways.

Soil salinity and the inseparable moisture content can be used to determine fertilizer migration dynamics within a soil profile.

It was in recognition of the described shortcomings of current methods of soil moisture and salinity measurements that the following device and installation procedure is proposed.

In summary, the inventors have developed a method and means capable of measuring and tracking the soil matric potential and soil salinity in a diverse range of soil types.

The apparatus and method aims to provide advantages over existing technology with one or more of the following attributes:

1. Increased accuracy and precision
2. Increased measurement range
3. Increased measurement resolution
4. Useable in range of soil types
5. No need for calibration (uses one factory calibration and a unique data processing model)
6. Able to monitor almost continuously
7. Instant useability
8. Reduced lag time
9. Simplified Installation
10. Sensor to be maintenance free
11. Depth compensating (no calibration)
12. Sensor to be frost proof
13. Profile measurement approach
14. Does not attract roots that may adversely affect or skew recorded data
15. Measures soil solution salinity simultaneously with soil moisture
16. Measures soil solution salinity (or pore water salinity) simultaneously with soil matric potential
17. Measures pore water salinity that is corrected for changing soil moisture conditions (matric potential)
18. No site destruction if sensor needs to be replaced To remove the need to calibrate a particular soil salinity sensor to measure soil salinity in hundreds of different soil types, the invention in a preferred arrangement provides for only one specific sensor calibration equation. This calibration equation is applicable to all manufactured sensors after sensor normalisation. The sensor is calibrated for matric potential and soil solution salinity (pore water salinity) in the specific media only and not for the surrounding soil with which the media maintains hydraulic contact and moisture exchange.

The inventors described herein is a method and means for measuring the soil water content and soil salinity in a single medium for which the determination of soil matric potential is merely a look up table exercise. The combination of sensor and medium is calibrated once and holds true for the period of use of the medium.

This approach is reliant on the medium having the characteristic of allowing the available soil moisture solutes to migrate into and out of the surrounding soil.

Furthermore, it is important that the field of influence of the sensor for measuring soil moisture and salinity is located wholly within the specified media. For sensors that use electromagnetic techniques that are used to determine soil moisture and salinity, the field of influence of the radiated electromagnetic radiation preferably remains totally within the volume of the media.

The use of a specified media guarantees that the measurements taken by the sensor and the data processing model, calibrated uniquely for the specified media, provide an accurate value of the soil matric potential of the media. According to the model, the soil in hydraulic contact with it has the same matric potential. Furthermore, the volumetric water content of the media, and hence, the salinity of the soil solution entering the media can be simultaneously measured.

The inventors have developed an arrangement of elements that, when used in a predetermined manner provide a way of measuring the matric potential and the associated measured volumetric soil water content of the medium (to derive matric potential) as well as the salinity of the soil solution entering the medium.

The clear advantage of such an apparatus and method is that only one combination of elements (elements being sensors, media and data processing model) need to be calibrated. That calibration is done in the laboratory, on the type of medium to be used and the resultant calibration equation is then relevant to all sensors produced (for that particular physical construction). The medium is arranged so that its moisture migration characteristics make the model useable in most soil types. Further more this apparatus and arrangement relies not upon sensing matric potential using the tensiometer principle but by sensing the total volumetric soil water content of the medium using a maintenance free and measurement range insensitive electromagnetic sensor. The calculation of the matric potential of the soil is done using a previously derived soil water release curve (calibration equation) derived for the media.

Most usefully, the apparatus does not need adjustments or corrections of any type between usage in a wide variety of different soil types. At the site, the pre-calibrated apparatus, including the predetermined media is merely installed. Due to automated measurement and data collection techniques, useful data for presentation to the user can be collected within an appropriate time and without any undue lag caused by the measurement devices operation. The measurement results are provided in well-recognized units, namely matric potential in kilopascals (kPa) and soil solution salinity in milli-Siemens per centimeter ($mS\ cm^{-1}$).

BRIEF DESCRIPTION OF THE INVENTION

In a broad aspect of the invention the soil parameter measurement method comprising the steps of:
a) locating a capacitive based soil moisture sensor in, or locating a said sensor adjacent to, a predetermined moisture migration medium of sufficient volume about said sensor such that said medium substantially occupies the field of influence of said sensor, and said medium is located in moisture and solute communication with soil to be measured by said sensor, and
b) measuring the complex dielectric constant of the medium for deriving the volumetric water content of said medium using said sensor, and processing said measurement to determine the matric potential of said medium and soil.

In a further aspect of the invention a soil characteristic measurement arrangement comprises a capacitive based soil moisture sensor having a field of influence, a predetermined moisture migration medium located in a volume surrounded by said sensor so that the medium occupies the field of influence of said sensor, and said medium is in moisture communication with said soil, wherein a) said sensor and predetermined medium is located in the soil, of which one or more characteristics of said soil is to be measured; and b) measuring the complex dielectric constant of said medium for deriving the volumetric water content of said medium using said sensor, and processing said measurement to determine the matric potential of said moisture and soil.

In yet a further aspect of the invention a mixture of compounds suitable for locating in soil and also suitable for allowing the migration of water and solutes from said surrounding soil and for the co-location of one or more sensors for measuring the soil water and salinity of said surrounding soil comprises diatomaceous earth or fine sand or fine glass beads or others suitable elements or a compound thereof.

In a yet a further aspect of the invention a capacitive sensor is located on the outside of a radio frequency permeable and solution permeable container filled with a migration medium adapted for the measurement of matric potential, soil water content and salinity of the medium and soil. This embodiment could be applied to a configuration where the soil to be measured is within a volume contained within the migration medium.

Specific embodiments of the invention will now be described in some further detail with reference to and as illustrated in the accompanying figures. These embodiments are illustrative, and not meant to be restrictive of the scope of the invention. Suggestions and descriptions of other embodiments may be included within the scope of the invention but they may not be illustrated in the accompanying figures or alternatively features of the invention may be shown in the figures but not described in the specification.

DETAILED DESCRIPTION OF EMBODIMENTS OF THE INVENTION

Figure 1:
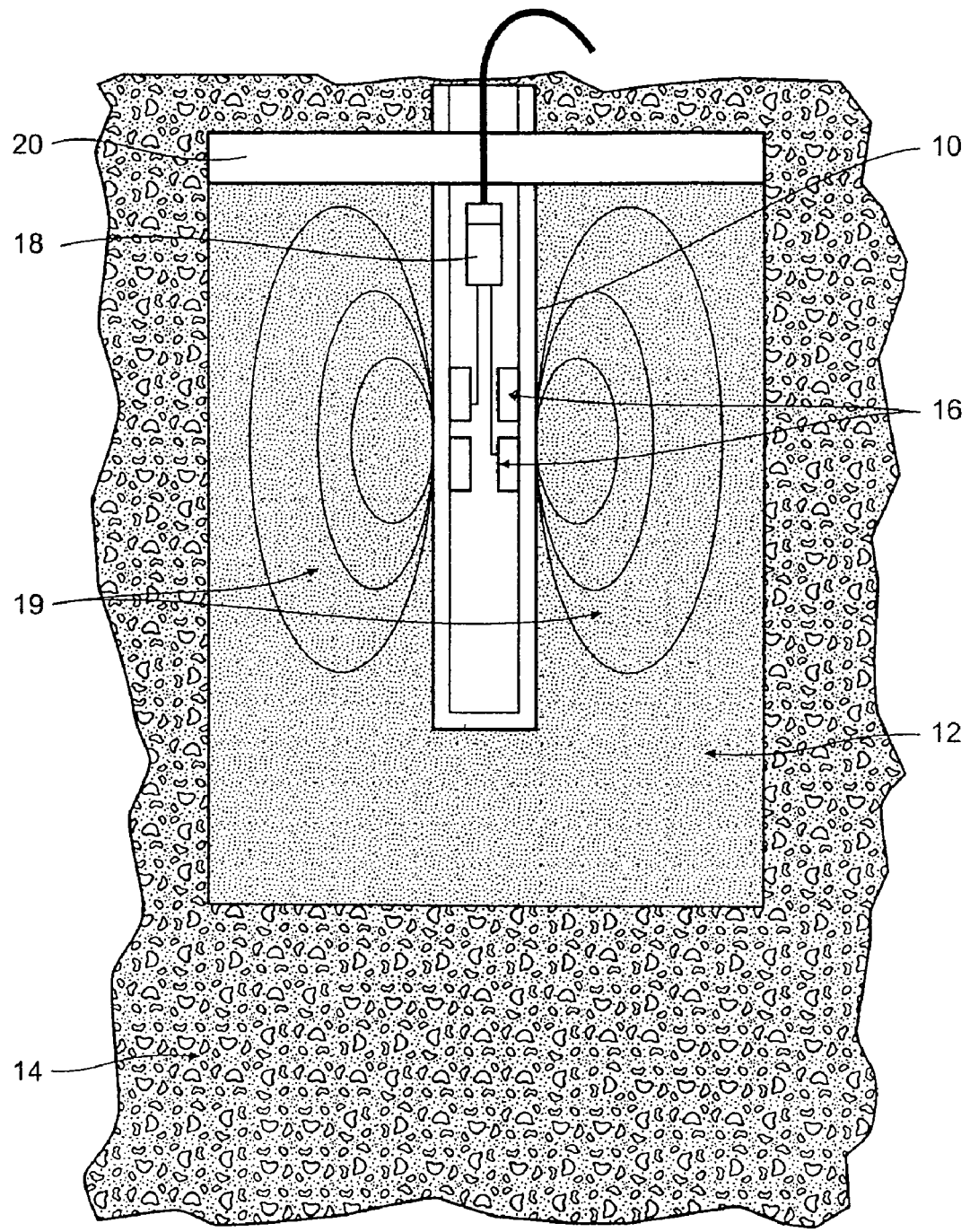
FIG. 1 depicts a single coil/migration medium installation in surrounding soil according to the invention.

FIG. 1 depicts a sensor 10 located in a single soil/compound installation 12 that itself is located in the soil 14 the moisture content and salinity characteristics of which are to be measured. Each of the elements described above is depicted in cross-section in FIG. 1 but the three-dimensional features can be readily implied.

The sensor in this embodiment is of the capacitive type, an example of which is disclosed in U.S. Pat. No. 5,418,466 the assignee of which is also the assignee of the patent associated with this specification. However, any sensor that uses electromagnetic radiation for providing soil moisture and salinity measurement capability can be used.

The sensor used in this embodiment relates to a device capable of providing moisture and salinity measurement. In particular to a sensor and its method of use that provides values for the complex dielectric constant of a medium. The values then need to be converted to volumetric soil moisture content (mm), soil matric potential $\psi$ in kPa and soil salinity in deci-Siemens per centimeter (dS/cm).

A sensor apparatus comprising a pair of capacitor elements (conductive rings 16) is arranged (shown in cross-section in FIG. 1) in a tuned circuit 18. Details of the tuned circuit will be known to those skilled in the art and general details of the circuit can be obtained from the previously mentioned U.S. Pat. No. 5,418,466.

The sensor described in the U.S. Pat. No. 5,418,466 uses two metallic rings as the plates of a capacitive element (C). The rings form a part of a LC oscillator whereby it oscillates at a frequency dependent on the values of L (inductance) and C (capacitance). If C is constant as is L in an LC circuit its resonant frequency f is inversely proportional to the permittivity of the surrounding medium. Permittivity is the ability of the medium to resist the formation of an electric field within it. Conversely, the dielectric constant of a material is a measure of how much electrostatic energy can be stored per unit volume when a unit voltage is applied to the medium.

The capacitance of the sensor is a function of the area of the sensor rings, their distance apart and the dielectric material near the rings. In the case of the sensor, the ring area and distance apart are fixed therefore the capacitance (C) is simply a function of the dielectric constant of the surrounding material which in the embodiment according to the invention is a moisture migration medium. If the inductance (L) is fixed, the frequency of oscillation is only a function of capacitance (C), which (as stated) is only a function of the dielectric material. So as the moisture content of the dielectric material changes so does the dielectric constant of the material therefore the frequency of oscillation is related to changes in soil moisture content.

Switching between the two frequency modes of the sensor is achieved by switching between two fixed inductors connected to the LC oscillator. The oscillator then oscillates within two different frequency bands (above and below 27 Mhz) and varies in those bands depending on the dielectric constant of the material near the rings (i.e. the soil). Operating in one mode (i.e. preferably at 150 Mhz which is well above 27 Mhz) the effect of varying salinity content results in a negligible effect on frequency of oscillation therefore the output of the oscillator is primarily dependant on the soil moisture. Operating in the other mode (i.e. preferably 5 Mhz which is well below 27 Mhz) the frequency of oscillation is dependent on not only soil moisture changes (as in the first mode) but is also dependent in part on changing salinity. Simplistically, if the response from first mode were taken away from the response of the second mode then the result would be an indication of salinity content of the soil.

A profile of the distribution of soil moisture and salinity is obtained by locating multiple sensors at various depths, typically 10 centimeters apart in a coaxial array. In the moisture and salinity measurement arrangement of this embodiment, the sensors are installed on a circuit board. The board acts also as a circuit board which can be inserted and removed in and from a hollow tube that is to be located into a predetermined medium itself located in the soil to be measured. Measurements are more likely to represent the actual characteristics of the soil as the medium readily adopts the soil matric potential of the surrounding soil. This is very unlike existing and prior sensor arrangements. Most prior sensor positioning arrangements are unlikely to accurately measure adjacent soil characteristics because of their tendency to create air gaps between the sensor and the surrounding soil.

To provide a compound that need only be calibrated with the chosen sensor once, the immediately surrounding volume is supplied to the user of the system as a pre-mixed material or compound that is chosen to offer a known moisture migration medium. The supply of the material or compound in this manner is merely for convenience as the ingredients may be separately obtainable and available for use or mixing by the user on site. It is preferable that the medium includes one or more of the following ingredients:
1) Diatomaceous Earth
2) Fine sand
3) Small diameter beads (eg glass)
4) Artificial grains, beads of suitable shape
5) Other (possibly small quantities of Bentonite plus other material/s)

The ingredient or a compound of two or more ingredients is preferably provided in a semi-moist state and is placed by the user into a prepared cylindrical hole about a cylindrical sensor. The volume of the hole is, as described previously, large enough so as to envelope the field of influence 19 of the sensors' electromagnetic radiation. In this embodiment, the cylindrical hole is about 20 cm in radius for the particular frequencies used of 1 MHz and 150 MHz. However, the field of influence 19 is electromagnetic and clearly its power is attenuated in the medium to different degrees in different mediums. It has been experimentally established by the inventors that at the high frequency, 95% of the attenuation of the signal occurs in the first 4 cm radius of the medium, while 99% of the attenuation occurs in the first 10 cm radius of the medium. Hence, use in this embodiment of a 20 cm radius.

The pre-mixed medium need not be compacted but may be tamped lightly to level the top surface. The ingredient or compound can be considered a hydraulic migration medium through which moisture in the surrounding soil about the sensor arrangement flows into or out of, given that the moisture will move in accordance with the various forces discussed previously. It will take some time for equilibrium of these forces and this will depend on the existing level of moisture in the soil.

Located on the top of the now mostly filled hole is a barrier 20 of disc-like shape. The barrier is substantially moisture impervious and positioned so as to prevent water resulting from rain or irrigation events from migrating directly from above the ground into the medium surrounding the sensor. The barrier can be of plastic and supplied with the kit of items that is provided to the user or can be created on site by the user with a material such as Bentonite for example.

Consequently, the hydraulic migration medium will only contain moisture and any solutes (typically of fertiliser and other salts) that migrate from the surrounding soil.

Using a migration medium that interfaces directly to the soil being tested avoids the use of semi-permeable membranes as is commonly used with other devices and sensors. Such membranes exhibit osmotic effects that concentrate liquid on one side and dilute liquid on the other which adversely affects the measurements being made.

Figure 2:
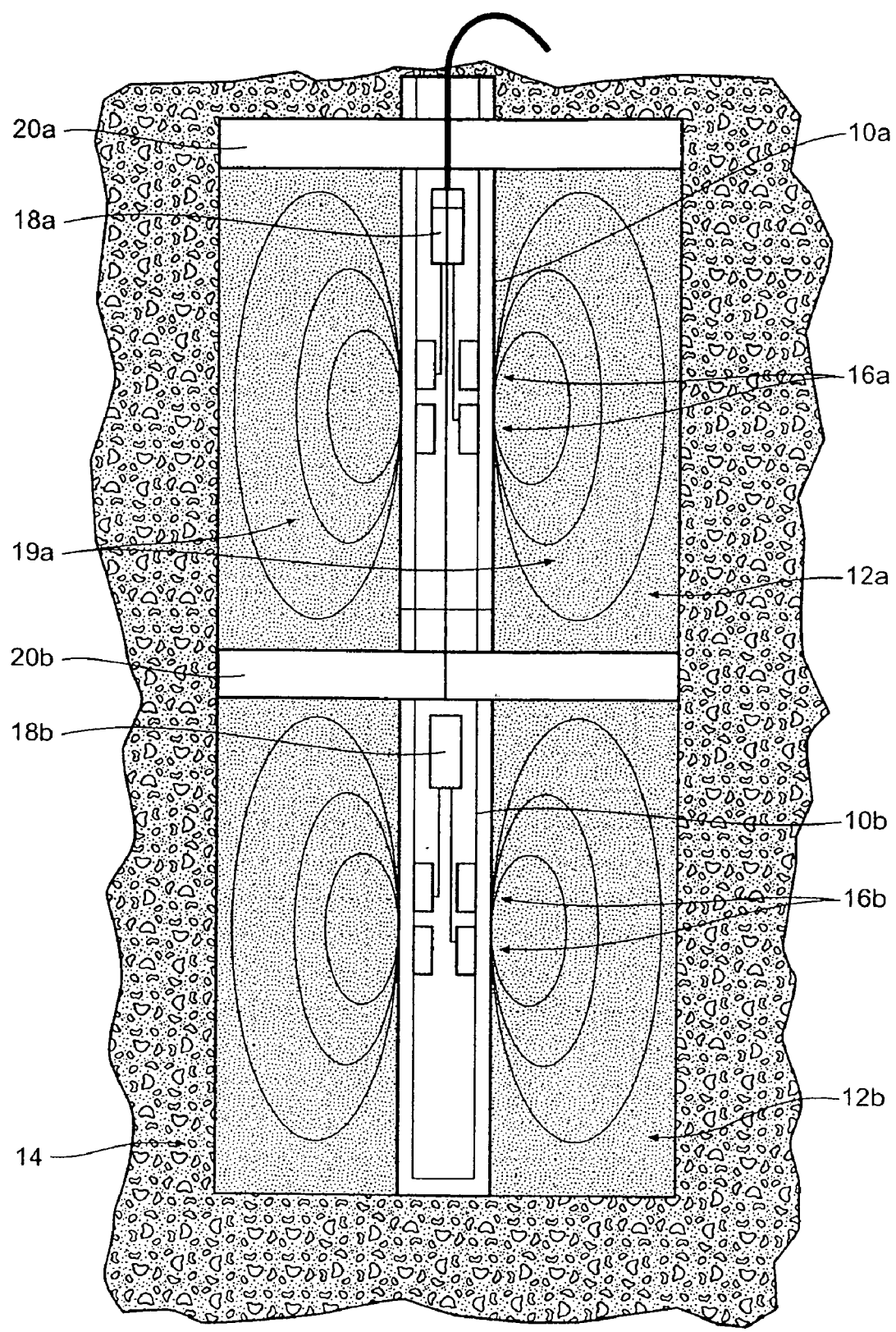
FIG. 2 depicts a multiple coil/migration medium installation in surrounding soil according to the invention.

FIG. 2 depicts two such sensors and mediums in a vertically spaced coaxial array. Like elements of FIG. 1 are depicted in FIG. 2 and the upper sensor and medium is distinguished from the lower sensor and medium by the a and b suffix respectively.

The importance of interfacial polarization effects (displacement of charges) in heterogeneous materials such as moist soil has been recognized as a distorting characteristic that will affect the measurement of soil moisture using capacitive elements at certain frequencies. It has been found that the relaxation frequency of the relatively macroscopic electric dipoles associated with interfacial polarization occurs at frequencies less than 27 Mhz.

Therefore the sensor described in the earlier mentioned U.S. Pat. No. 5,418,466 by the applicant, in one mode of operation, uses frequencies well above 27 Mhz when measuring the complex dielectric constant so that the dipole interaction does not contribute to the complex dielectric constant detected by the sensor. In another mode of operation, the sensor uses a frequency below 27 Mhz.

Furthermore at frequencies above 27 Mhz the complex dielectric constant detected by the sensor is primarily a function of soil water content and typically also of soil particle shape, porosity and the geometrical arrangement of particles.

The relation between water content, conductivity, and complex dielectric constant at frequencies below 27 Mhz is a strong function of soil type, temperature and the solute concentration of the soil solution.

Thus, it is possible to quantify changes over time in the soil conductivity by measuring the complex dielectric constant at frequencies above 27 Mhz (BF) and frequencies below 27 Mhz (LF). During those measurements of soil moisture level the sensor is at a fixed position in the soil. With two parameters being held constant (soil moisture and soil type) changes in the relative complex dielectric constant can only be caused boy a variation in two other parameters. These variables are conductance as a function of the dissolved salts in soil water per unit volume and the temperature of the surrounding medium.

There is yet some speculation by the inventors that the use of frequencies above and below 27 Mhz is appropriate for all solute concentrations particularly in high salinity environments. However, by way of example such an arrangement is used in this specification.

In this invention preferentially the described dual mode frequency sensor is used, however it is located within a hydraulic migration medium such that its field of influence is also contained within the volume of the medium. In turn the medium is in contact with the soil to be measured, allowing, if the energy conditions are appropriate, for the soil solutions to migrate into or out of the hydraulic migration medium until equilibrium is reached.

Calculation Steps

Figure 4:
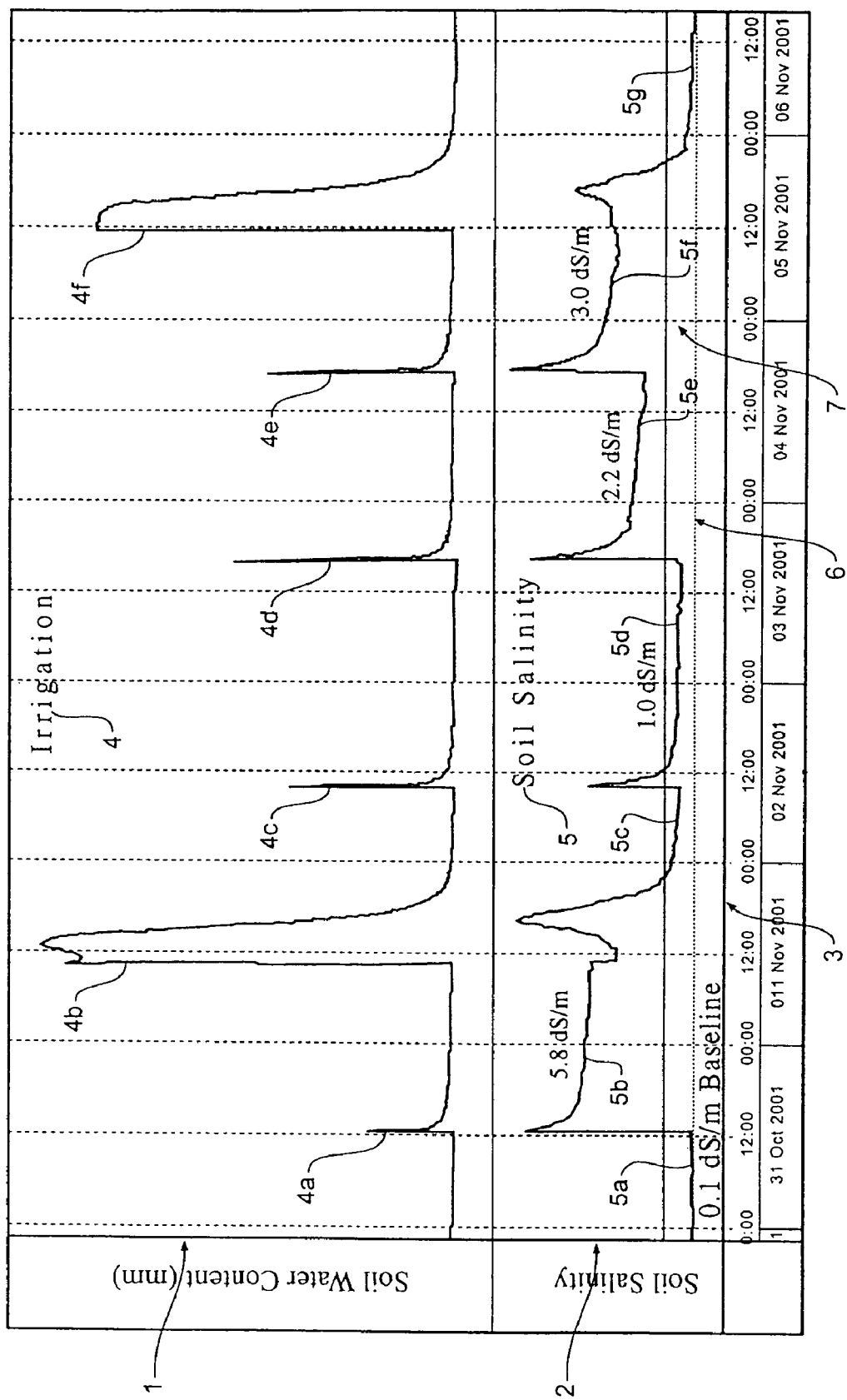
FIG. 4 depicts a printout of soil moisture and salinity showing trends of soil water and salinity content over time.
Figure 5A:
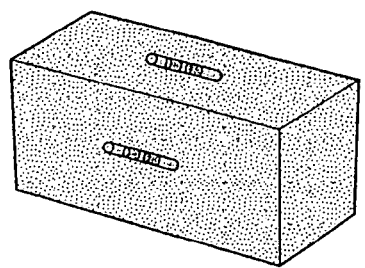
FIG. 5 depicts a variety of migration medium shapes.
Figure 5B:
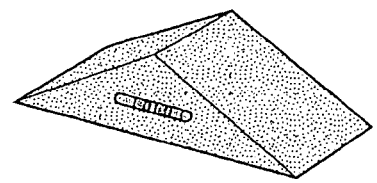
Figure 5C:
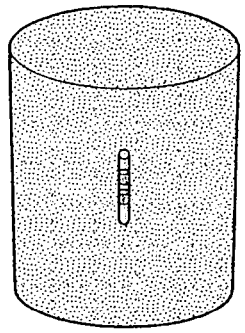
Figure 5D:
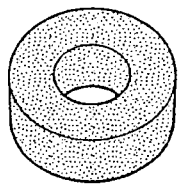
Figure 5E:
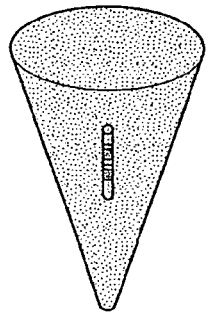
Figure 5F:
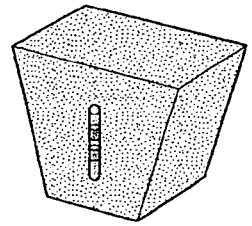
Figure 5G:
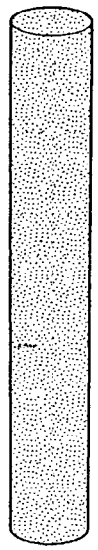
Figure 5H:
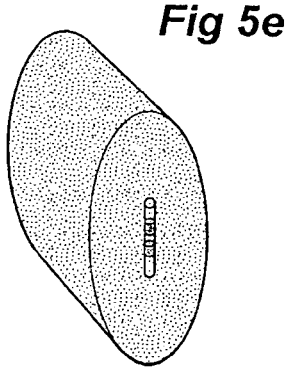
Figure 5I:
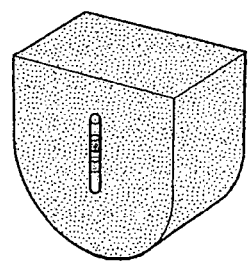
Figure 6A:
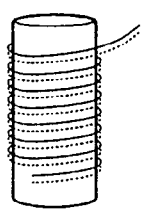
FIG. 6 depicts a variety of sensor configurations.
Figure 6B:
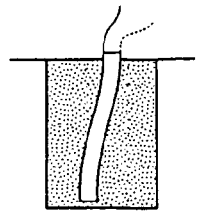
Figure 6C:
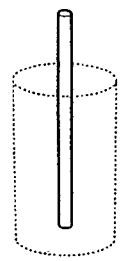
Figure 6D:
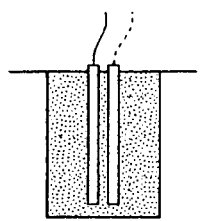
Figure 6E:
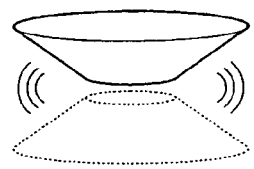
Figure 6F:
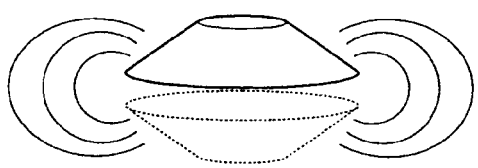
Figure 6G:
Figure 6H:
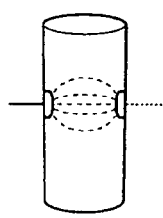
Figure 6I:
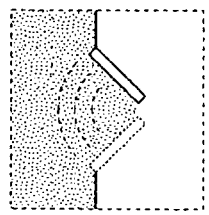
Figure 6J:
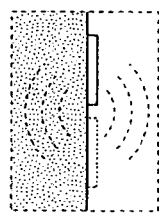
Figure 6K:
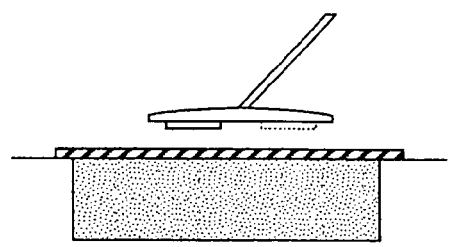
Figure 6L:
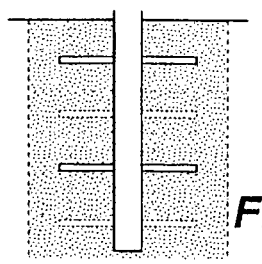

Referring to FIG. 4 the HF measurement of the sensor indicates the volumetric water content $\Theta$ of the hydraulic migration medium. It does not represent the volumetric water content of the surrounding soil at any given point in time because the texture and the resulting volumetric media water storage capacity of the hydraulic migration medium is different to the texture and resulting volumetric water storage capacity of the soil, at the point of the same matric potential measurement in the hydraulic migration medium and soil.

However, the energy level or the matric potential of the water in the hydraulic migration material is the same as the matric potential of the water contained within the surrounding soil when energy equilibrium between these two media is reached.

Measuring matric potential inside the hydraulic migration medium then reflects the matric potential of the soil from which plants have to overcome to extract water. This is similar in principle to measuring matric potential or negative suction inside a tensiometer to determine the matric potential of the soil.

The functional relationship between volumetric water content $\Theta$ of a soil and matric potential of a soil $\psi$ for many soil types are described by soil specific hyperbolic equations termed soil water release curves. Because of the almost infinite combination of soil types around the world, many soil water release curves have yet to be determined. If a soil water release curve for a media is known, it is possible to determine either volumetric water content $\theta$ using the $\psi$ parameter or determine matric potential $\psi$ using the $\theta$ parameter.

In this invention a HF measurement will be used as a function of $\psi$ determined for the sensor hydraulic migration material in the laboratory using a hanging water column and a pressure plate apparatus. This approach provides for the establishment of a HF and $\psi$ functional relationship to cover a range from 0 kPa to a limit yet to be determined. Such a limit is currently approximately 15 bar as determined by the capability of pressure apparatus that will be used to derive the soil water release curve.

With two parameters being held constant (sensor medium and matrix potential measured at high frequency) changes in the relative dielectric constant can only be caused by a variation in the two other parameters.

The variable parameters are conductance as a function of the dissolved salt in the sensor hydraulic migration medium (soil) water per unit volume and the temperature of the surrounding medium. Both are respectively measured using the LF mode of the sensor and an integrated temperature sensor. Osmotic potential can be ignored, as there are no semipermeable walls between the hydraulic migration material and the soil.

The hydraulic migration material is permeable to both water and solutes. The solutes in the soil solution diffuse freely into the hydraulic migration material so the water inside the hydraulic migration material acquires the same solute composition and concentration (osmotic potential) as the soil water.

Holding the matric potential constant requires a correction using another two dimensions. Namely, the matric potential correction for gravity potential (elevation) and matric potential hysteresis effects in relation to the volumetric water content of the hydraulic migration media. The correction is achieved using multi-dimensional calibration models.

The inclusion of the ability to measure and account for matric potential, gravity potential (elevation) and hysteresis effects constitutes a further development of data analysis techniques disclosed in U.S. Pat. No. 5,418,466. This advance allows the same sensor type and a particular installation technique to be use in a wide range of soil types to measure matric potential, volumetric soil water content (if the soil specific soil water release curve is known) and soil solution salinity. A calibrated multi-dimensional data processing model is required since the sensor is calibrated for a known migration medium that is replicated in the field. The data processing flow is as follows:

Data Processing Description:

The sensor takes raw counts at a frequency above 27 Mhz (HF) and raw counts at a frequency below 27 Mhz (LF). Raw counts of both frequency measurements are normalised using the equation:

Scaled Frequency (SF)=(Air count−Migration medium count) over (Air count−Water count).

Normalised high frequency values are denoted $SF_H$ and normalised low frequency values are denoted $SF_L$.

$SF_H$ is calibrated versus the volumetric water content $\theta$ of the hydraulic migration medium.

$SF_H$ is also calibrated with matric potential $\psi$ of the hydraulic migration medium (Function B) and forms one of the final calculated data output i.e. matric potential.

Soil solution salinity $EC_w$ (pore water salinity), the final calculated data output, is calculated as a function of the following variables:

1. $\Psi=f1(SF_H)$
2. $ECw=f2(\Psi,SF_L)$

To add temperature correction to the data processing model, temperature readings are calibrated with volumetric water content $\theta$ and hence $HF_{SF}$ (Function A) and hence matric potential $\psi$.

Including temperature t as another variable into the processing model yields the following functions:

3. $\Psi=f1(SF_H,t)$
4. $ECw=f2(\Psi,SF_L, t)$

Four variables determine soil salinity:

1. Soil mineralogy
2. Soil solute concentration of the soil solution
3. Soil matric potential
4. Soil temperature The impact of soil mineralogy (variable 1) in the calculation of soil salinity has been excluded using a hydraulic migration medium. Soil matric potential (variable 3) is determined using the high frequency measurement mode of the sensor and a specific soil water release curve of the hydraulic migration medium. Soil solute concentration (variable 2) is measured by the low frequency measurement mode of the sensor and corrected for soil matric potential (variable 3) and soil temperature (variable 4) to arrive at an accurate soil solute concentration coupled with an accurate soil matric potential measurement.

Figure 3:
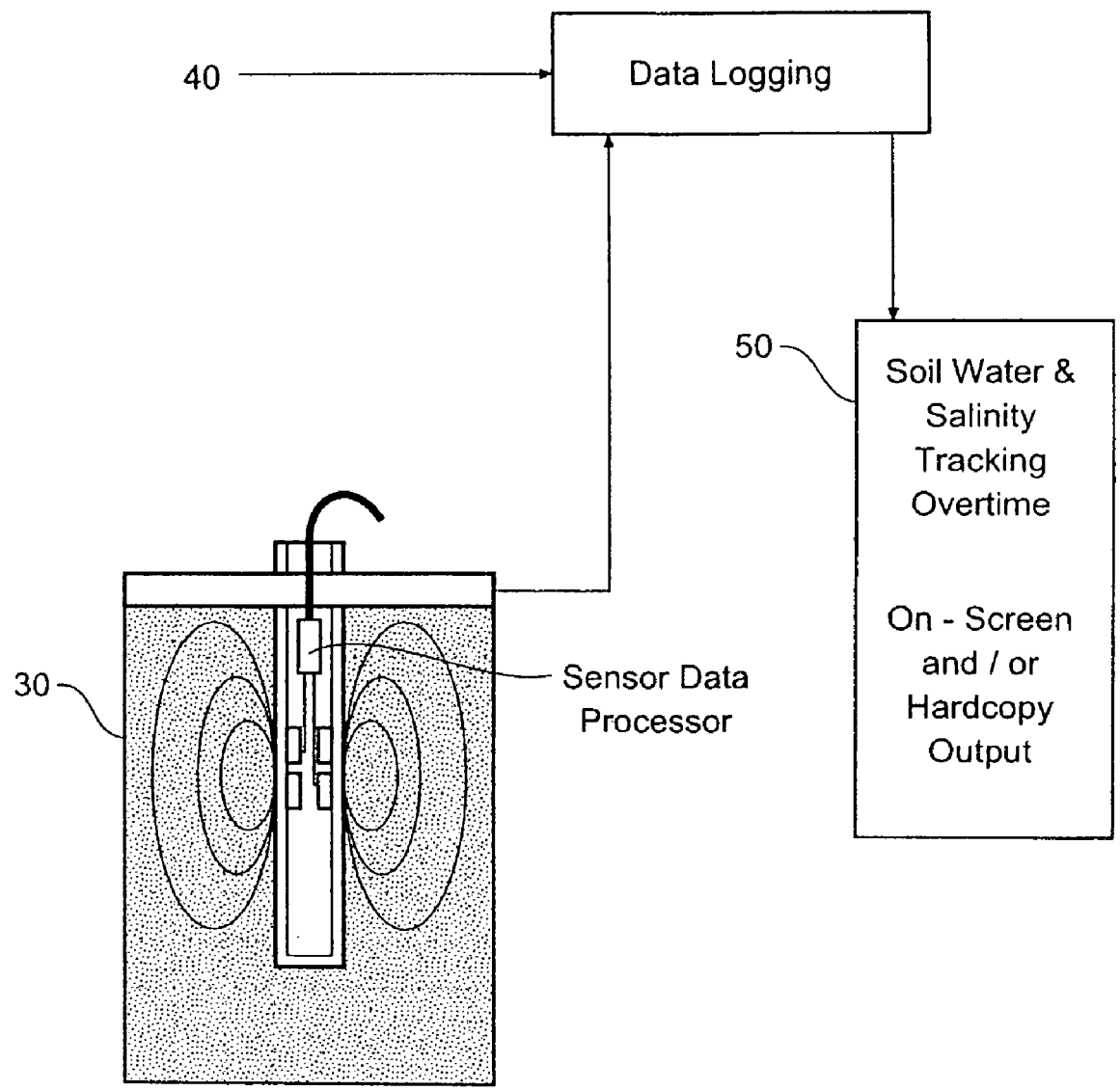
FIG. 3 is a pictorial representation of devices for detection and display of soil moisture and salinity parameters.

FIG. 3 depicts a pictorial representation of various devices used in the detection and display of soil moisture and salinity parameters such as volumetric soil water content and salinity.

The arrangement of sensor and surrounding hydraulic migration medium depicted in FIG. 1 is also depicted at 30 in FIG. 3. The sensor is the source of signals created by the sensor apparatus (16,18) in the two modes of operation. In this embodiment, the sensor described has two modes but other sensors may not need to work in such a fashion. The data generated by the sensor is sent to a data processing device 40, which, in this embodiment is a data-logging device. Data loggers are well known in the field of remote sensor usage and need not be described in detail herein. In this embodiment, the type of data processing required is described in U.S. Pat. No. 5,418,466. However, note that the processing required could be done at the same location as the sensor or it could be done at a remote location such as a computer in the residence or office of the user. The processing could be done on the fly or it could be done in preparation for the generation of the graphical output made available to the final user of the arrangement. If any processing is done remotely then there exist many known methods for communicating the data to that remote location.

Of ultimate value to the user of the apparatus is the provision of trend information in the form of a graph 50, an example of which is given in FIG. 4.

FIG. 4 depicts an example of a graph that an end user would use to make irrigation and fertiliser management decisions.

The graph depicts parameter 1 being soil water content and parameter 2 being soil salinity plotted against a common time axis 3.

The units of soil water content $\theta$ are given in mm soil water per 100 mm depth of hydraulic migration material. Alternatively, units can be converted into matric potential $\psi$ using the specific soil water release curve for the hydraulic migration medium. The exact scale is omitted as it varies with hydraulic migration material type.

The units of soil salinity 2 can be presented as dS/m (deci Siemens per meter). They can also be expressed as $\mu S\ cm^{-1}$ (micro-Siemens per centimeter) and as ppm (parts per million of Total Dissolved Solids). 1 dS $m^{-1}$=1000 EC (Electrical Conductivity measured in $\mu S\ cm^{-1}$)=640 ppm. The exact scale is omitted as it varies with hydraulic migration material type.

The unit of time axis 3 is shown as hours and days. Time can also be expressed as seconds, minutes, days, weeks, months or years.

Multiple irrigation events 4a to 4f are plotted using the axis of soil water content 1 and time axis 3.

Multiple resulting salinity levels 5a to 5g (after each irrigation event) are plotted using the axis of soil salinity 2 and time axis 3.

The soil salinity level 5a on October 31 before 12.00 p.m. was very low being 0.1 dS $m^{-1}$ (salinity of rain water) and is used as a lower salinity baseline 6 against which salinity rises and falls can be measured.

The soil salinity threshold 7 is crop specific and indicates the average root zone salinity at which salts begin to affect crop or pasture growth. Beyond this value crop yield decline can be expected. In this example the soil salinity threshold has been set to 1.5 dS $m^{-1}$ which is the critical threshold for White Clover.

Other important soil salinity thresholds (not shown here) can indicate the 25%, 50% and 75% yield loss threshold for a particular crop. For example, a 3.6 dS $m^{-1}$ soil salinity threshold indicates 25% yield loss threshold for White Clover.

The irrigation 4a applied shortly after 12.00 p.m. on October 31 contained salts measuring 5.8 dS $m^{-1}$ and created a 5.8 dS $m^{-1}$ level 5b. This soil salinity level is severely damaging to most agricultural crops.

The irrigation 4b on November 1 was applied as a leaching irrigation using distilled water to flush out any soil salts. This irrigation 4b caused a steep drop in the salinity that levels out at a level 5c on November 2 which is close to the base salinity level 7.

Irrigation 4c applied on November 2 contained a salinity level of 1.0 dS m$^{-1}$ and caused only a very slight rise in the resulting salinity level 5d.

Irrigation 4d applied on November 3 contained a salinity of 2.2 dS m$^{-1}$ raising the salinity level 5e above the critical soil salinity threshold 7 for White Clover.

Irrigation 4e at 3.0 dS m$^{-1}$ salinity applied on November 4 continued to increase the salinity level 5f.

Another leaching irrigation event 4f using distilled water applied on November 5 caused the soil salinity level 5g to drop below the critical soil salinity threshold 7 and continued to drop to level out just slightly above the base salinity level 6.

The graphical representation provided in FIG. 4 allows the user to view the interaction of soil moisture and soil salinity simultaneously on a near continuous basis at a particular depth level in the soil profile when multiple sensor arrangements are used in vertically spaced co-axial alignment a depicted in FIG. 2.

FIG. 5 depicts a variety of shapes of the hydraulic migration media in which a capacitive sensor can be embedded, so that its sphere of influence is substantially contained within the hydraulic migration medium.

The shapes depicted in FIG. 5 are generic. It is considered that the principle of the invention is adequately disclosed in this specification. Therefore, the choice of the actual shape to be used in most situations will likely be of the generic shapes depicted. Alternatively, the shape may consist of a combination of one or more of them or variations thereof or a completely different shape. The examples provided are not meant to limit the scope of the invention.

The following is a short explanation of the shapes suitable for different measurement applications:

1) A square shape can be used at the soil surface to determine surface moisture and salinity conditions. A rectangular hole is dug into the soil and the sensor can be embedded in the medium or mounted on a flat plastic surface forming a cover over the shaped hydraulic migration medium (HAM).

2) A triangular shape can be used by direct placement of the hydraulic migration medium on the soil surface to make the device more responsive to soil surface moisture and salinity conditions. A plastic lid taking the shape of a cover, in this example the shape of a roof would cover the HMM. The sensor could be embedded in the HMM or mounted onto the roof material internal of the shape. Water running off the roof would be running to the sides of the measuring device and penetrate into the soil so that it can be measured also.

3) A cylindrical shape is used by auguring a hole into the soil and filling it with HMM. The sensor is placed coaxial of the HMM cylindrical shape.

4) A solid ring shape of the HMM is used within a potting container where the hole of the HMM ring is filled with a growing medium (perlite, pumice, potting mix etc.) The arrangement of capacitive elements (not shown here) can either be on the outside of the solid ring shape or located on the inside and outside of the shape.

5) Inserting a metal tip into the soil surface and filling it with HMM creates a funnel shape. The sensor can be placed in the HMM or placed in a portable monitoring device that would be placed on top of the HMM funnel.

6,8,9) Soil drenching to create interceptor channels to monitor potential path flows of water and salinity in the soil profile and landscape would be a reason to create and use shapes 6, 8 and 9.

7) Shape 7 is cylindrical the same as shape 3 however the arrangement of sensor plates (not shown) is on the outside of the cylinder. This arrangement is useful if the HMM is contained in a tube which is in hydraulic contact with the soil to be measured assuming the sensor plates 16 can be arranged to allow relatively unimpeded migration of the moisture in the surrounding soil into and out of the HMM.

FIG. 6 depicts a variety of sensor shapes showing how different sensors can be used in different ways in the same and different HMM configurations. Since in these examples a capacitive sensor is used, at a minimum there needs to be two conductive elements. As can be seen the elements can be wire, ribbon or plate-like and other arrangements of capacitive elements are possible. In FIG. 6 one portion of the two part sensor is shown in solid lines and the other portion is shown is dotted lines.

The elements can be arranged so that the HMM substantially encompasses the field of radiation (electromagnetic radiation (EM)) between the elements and thus forms the dielectric that is affected by the soil moisture and salinity that migrates into it as a result of the energy equalisation that occurs between the HMM and the surrounding soil. However, in some cases only a portion of the EM radiation generated would be confined within the volume of the HMM. The remaining EM radiation in those applications should be arranged to be in free air or contained within a salinity and moisture inert material, in,any case a known media which is substantially a non-water or salinity adsorbent material eg. air, plastic, ceramics, etc.

It will be appreciated by those skilled in the art, that the invention is not restricted in its use to the particular application described. Neither is the present invention restricted in its preferred embodiment with regard to the particular elements and/or features described or depicted herein. It will be appreciated that various modifications can be made without departing from the principles of the invention. Therefore, the invention should be understood to include all such modifications within its scope.

The claims defining the invention are as follows:

1. A soil parameter measurement arrangement comprises:
   a capacitive based soil moisture sensor having a field of influence,
   a predetermined moisture migration medium located in a volume adjacent said sensor so that the medium substantially occupies the field of influence of said sensor wherein said medium is in moisture and solute communication with the soil to be measured, and said sensor measures the complex dielectric constant of the medium for deriving the soil moisture of said medium and soil.

2. A soil parameter measurement arrangement according to claim 1 wherein said capacitive based soil moisture sensor derives the ionic concentration of the soil solution (salinity) of said medium.

3. A soil parameter measurement arrangement according to claim 1, wherein said predetermined medium contains diatomaceous earth or fine sand or fine glass beads or an artificial material or a compound thereof.

4. A soil parameter measurement arrangement according to claim 1, comprising a substantially moisture impervious barrier located above said moisture migration medium.

5. A soil parameter measurement arrangement according to claim 1, wherein two or more of said sensors are spaced a predetermined distance apart in an array, and said array is vertically orientated with said medium, both said array and medium being located in said soil so that said measurements provide a soil profile.

6. A soil parameter measurement method comprising the steps of:

a) locating a capacitive based soil moisture sensor in, or locating a said sensor adjacent to, a predetermined moisture migration medium of sufficient volume about said sensor such that said medium substantially occupies the field of influence of said sensor, and said medium is located in moisture and solute communication with soil to be measured by said sensor, and b) measuring the complex dielectric constant of the medium for deriving the volumetric water content of said medium using said sensor, and processing said measurement to determine the matric potential of said medium and soil.

7. A soil parameter measurement method according to claim 6 comprising further step of:

c) using said capacitive based soil moisture sensor to derive the ionic concentration of the soil solution (salinity) of said medium.

8. A soil parameter measurement method according to claim 6, comprising the further step of:

d) forming an empty volume in said soil to be measured and filling it with said sensor and a predetermined medium.

9. A soil parameter measurement method according to claim 7, comprising the further step of:

e) forming a substantially moisture impervious barrier above said moisture migration medium.

10. A soil parameter measurement method according to claim 7, wherein two or more of said sensors are spaced a predetermined distance apart in an array, and said array is vertically orientated with said medium, both said array and medium being located in said soil so that said measurements from said spaced sensors provide a soil profile.

11. A soil characteristic measurement arrangement comprises a capacitive based soil moisture sensor having a field of influence, a predetermined moisture migration medium located in a volume surrounded by said sensor so that the medium occupies the field of influence of said sensor, and said medium is in moisture and solute communication with said soil, wherein a) said sensor and predetermined medium is located in the soil, of which one or more characteristics of said soil is to be measured; and b) measuring the complex dielectric constant of said medium for deriving the volumetric water content of said medium using said sensor, and processing said measurement to determine the matric potential of said medium and soil.

12. A soil characteristic measurement arrangement according to claim 11 wherein said capacitive based soil moisture sensor derives the ionic concentration of the soil solution (salinity) of said medium.

13. A soil characteristic measurement arrangement according to claim 11, wherein said predetermined medium contains diatomaceous earth or fine sand or fine glass beads or an artificial material or a compound thereof.

14. A soil characteristic measurement arrangement according to claim 11, wherein said sensor is located on the outside of a electromagnetic energy permeable and solution permeable container filled with said predetermined medium wherein said sensor measures the volumetric soil water content and/or salinity of said medium.

15. A soil characteristic measurement arrangement according to claim 11, wherein an empty volume in said soil to be measured is formed and filled with said sensor and said predetermined medium.

* * * * *